(12) United States Patent
Qin

(10) Patent No.: US 10,024,861 B2
(45) Date of Patent: Jul. 17, 2018

(54) ELECTROCHEMILUMINESCENCE IMMUNOASSAY METHOD

(75) Inventor: Jun Qin, Beijing (CN)

(73) Assignee: BEIJING UNIDIAG TECHNOLOGY INC, Beijing (CN)

( * ) Notice: Subject to any disclaimer, the term of this patent is extended or adjusted under 35 U.S.C. 154(b) by 720 days.

(21) Appl. No.: 14/005,203

(22) PCT Filed: Mar. 13, 2012

(86) PCT No.: PCT/CN2012/072248
§ 371 (c)(1),
(2), (4) Date: Nov. 19, 2013

(87) PCT Pub. No.: WO2012/122929
PCT Pub. Date: Sep. 20, 2012

(65) Prior Publication Data
US 2014/0072963 A1  Mar. 13, 2014

(30) Foreign Application Priority Data
Mar. 16, 2011 (CN) .......................... 2011 1 0063893

(51) Int. Cl.
*G01N 33/58* (2006.01)

(52) U.S. Cl.
CPC ....... *G01N 33/582* (2013.01); *G01N 2458/40* (2013.01)

(58) Field of Classification Search
CPC .......................... G01N 33/582; G01N 2458/40
See application file for complete search history.

(56) References Cited

U.S. PATENT DOCUMENTS

| | | | | |
|---|---|---|---|---|
| 5,770,459 A * | 6/1998 | Massey | ................. | C07D 213/22 435/7.1 |
| 5,945,344 A * | 8/1999 | Hayes | ..................... | G01N 21/69 250/361 C |
| 7,205,117 B1 * | 4/2007 | Robertson | ............ | G01N 33/564 435/7.23 |
| 2008/0227219 A1 * | 9/2008 | Gamez | ................. | G01N 33/532 436/518 |
| 2010/0133118 A1 | 6/2010 | Sosnowski et al. | | |

FOREIGN PATENT DOCUMENTS

| | | |
|---|---|---|
| CN | 101246125 | 8/2008 |
| CN | 101318979 | 12/2008 |
| CN | 101532916 | 9/2009 |
| JP | 09184842 | 7/1997 |
| JP | 2009-534667 | 9/2009 |
| WO | WO 2007/121465 | 10/2007 |

OTHER PUBLICATIONS

"Development of Automated Immune Analysis," *Chinese Medical Journal*, vol. 6, Issue 1, Jan. 2006. (English summary of Chinese publication).
Liu et al., "Environmentally Friendly and Highly Sensitive Ruthenium(II) Tris(2,2'-bipyridyl) Electrochemiluminescent System Using 2-(Dibutylamino)ethanol as Co-Reactant," *Angew. Chem.*, 119(3):425-428, 2007.
PCT International Search Report and Written Opinion issued in International Patent Application No. PCT/CN2012/072248, dated May 24, 2012. (English translation of Chinese text).
Wei et al., "Chitosan-nanogold composite film modified electrochemiluminescent immunosensor for determination of human IgG," *Scientia Sinica Chimica*, 4(6):704-710, 2010. (English abstract of Chinese publication).
Liu et al., "Environmentally friendly and highly sensitive ruthenium(II) tris(2,2'-bipyridyl) electrochemluminescent system using 2-(dibutylamino)ethanol as co-reactant," *Angew. Chem. Int. Ed.*, 46(3):421-424, 2007.
Office Communication issued in Japanese Patent Application No. 2013-558296, dated Aug. 19, 2014. (English translation of Japanese text).
Wei et al., "Bis(2,2'-bipyridine)(5,6-epoxy-5,6-dihydro-[1,10] phenanthroline)ruthenium Synthesis and Electrochemical and Electrochemiluminescence Characterization," *Anal Chem.*, 80:5635-5639, 2008.
English translation of Office Communication issued in Korean Patent Application No. 10-2013-7027041, dated Dec. 19, 2014.
Rivera et al., "Rapid detection of Clostridium botulinum toxins A, B, E, and F in clinical samples, selected food matrices, and buffer using paramagnetic bead-based electrochemiluminescence detection," *Analytical Biochemistry*, 353(12):248-256, 2006.
Yan et al., "Rapid and sensitive immunomagnetic-electrochemiluminescent detection of P53 protein from human lung cancer," In: *Optics in Health Care and Biomedical Optics: Diagnostics and Treatment*, Britton Chance, Mingzhe Chen and Gilwon Yoon, Eds., Proceedings of SPIE, vol. 4916, pp. 134-139, 2002.

* cited by examiner

*Primary Examiner* — Andrea S Grossman
(74) *Attorney, Agent, or Firm* — Parker Highlander PLLC

(57) ABSTRACT

An electrochemiluminescence immunoassay method is disclosed and uses a full reaction of a Ru(bpy) marked protein-primary antibody, a biotinylated protein-secondary antibody to be tested, and a sample to be tested; addition of a Streptavidin-coated magnetic particle to form a complex comprising an antigen, an antibody, and a magnetic particle; adsorption to an electrode surface by the magnetic particle; addition of a dibutyl ethanolamine solution; and testing by an electrochemical method. Also disclosed is a corresponding electrochemiluminescence immunoassay detection kit.

2 Claims, 3 Drawing Sheets

ELECTROCHEMILUMINESCENCE IMMUNOASSAY METHOD

This application is a national phase application under 35 U.S.C. § 371 of International Application No. PCT/CN2012/072248, filed Mar. 13, 2012, which claims the priority of China Patent Application No. 201110063893.0, filed with the Patent Office of China on Mar. 16, 2011, entitled "ELECTROCHEMILUMINESCENCE IMMUNOASSAY METHOD", the contents of which are incorporated herein by reference in its entirety.

FIELD OF THE INVENTION

The present invention relates to the field of immunology, particularly to an electrochemiluminescence immunoassay method.

BACKGROUND OF THE INVENTION

Chemiluminescence immunoassay is a non-radioactive immunoassay produced using a labeling illuminant as a tracer signal, which has the advantages of high sensitivity, broad linear range, rapid analysis speed, simple operation, and ready for automation.

Currently, chemiluminescence immunoreagents commonly used in clinical practice are:

1. Reaction systems using alkaline phosphatase and horseradish peroxidase with luminol. The main disadvantage thereof is that the activities of alkaline phosphatase and horseradish peroxidase are greatly affected by temperature variation, and the experimental results are greatly affected by environmental variation.

2. Luminescence reactions using alkaline solution of acridinium ester and derivatives thereof with hydrogen peroxide. The main disadvantage is that it is a flash luminescence with short luminescence time, which can only be detected on a fully automated instrument. The mode for the calculation of the results is complex, and the experimental results are not stable.

3. Electro-chemiluminescence systems using ruthenium pyridine and tripropylamine.

Electro-chemiluminescence (ECL) reaction is a specific chemiluminescence reaction triggered by electrochemistry on the surface of an electrode. The conjugate of antigen-antibody complex and ruthenium pyridine is electrochemically excited by electrochemistry in the presence of tripropylamine, and a redox reaction occurs to emit photons, which can be collected by a photomultiplier tube. This process is performed repeatedly to produce plenty of photons, which enhance the optical signal. The labels commonly used in the electrochemiluminescence analysis are those which can bind to an antibody or an antigen molecule with different chemical structures, to produce a labeled antibody or antigen.

Ruthenium pyridine is water-soluble and highly stable, which ensures an efficient and stable electrochemiluminescence reaction and avoids the interference from background noise. Even when the molecular ratio of the binding of ruthenium pyridine to immunoglobulin exceeds 20, the solubility and the immunological activity of antibodies are not affected, the molecular weight and steric hindrance remain low, and thus even a small molecular nucleic acid can also be labeled.

The currently available electrochemiluminescence methods mainly employ tripropylamine (TPA) as a reactant. The disadvantages of tripropylamine are that the reaction is slow, the concentration is high, it is greatly affected by electrode material, the luminescence efficiency is limited, and it is not cost optimized.

SUMMARY OF THE INVENTION

The technical problem to be solved by the present invention is to provide an electrochemiluminescence immunoassay method with high luminescence efficiency and rapid reaction, and which is widely applicable.

In order to achieve the above purposes of the invention, the present invention provides the following technical solutions:

There is provided an electrochemiluminescence immunoassay method, comprising the following steps:

step 1: reacting a ruthenium pyridine-labeled primary antibody against the protein to be tested and a biotinylated secondary antibody against the protein to be tested being sufficiently reacted with a sample to be tested, or reacting a ruthenium pyridine-labeled antibody against the protein to be tested and a biotinylated protein to be tested being sufficiently reacted with a sample to be tested;

step 2: adding magnetic particles coated with streptavidin, allowing the reaction so as to form a complex comprising an antigen, an antibody and a magnetic particle, drawing the reaction liquid into a flow cell, in which the complex comprising an antigen, an antibody and a magnetic particle is adsorbed onto the surface of an electrode through the magnetic particle;

step 3: adding a dibutyl ethanolamine solution, starting the ECL reaction by applying voltage, and collecting the scanned optical signals by an optical detector;

step 4: formulating standard solutions in a gradient of concentrations, plotting a dose-response curve according to the logarithm of changes in the value of luminescence intensity and the logarithm of concentration, and obtaining the concentration of the protein to be tested in the sample to be tested by calculation.

The basic principle for ECL is that the luminescence substrate and the component in the reaction lose electrons on the surface of an electrode, so as to be oxidized. The electron donor loses a $H^+$ to become a strong reducing agent, which reduces the luminescence substrate to the excited state, and then the luminescence substrate releases photons to return to the ground state. This process is performed repeatedly on the surface of the electrode, and photons are continually released to keep the substrate concentration constant.

The disadvantages of tripropylamine (TPA) are that the reaction is slow, the concentration is high, and it is greatly affected by electrode material. The luminescence efficiency of dibutyl ethanolamine is obviously better than that of the TPA, and a diagram comparing the luminescence intensities thereof on a platinum electrode and on a gold electrode is shown in FIG. 5. Dibutyl ethanolamine (DBAE) is selected as the co-reactant, and ruthenium pyridine is employed as a label in the present invention in order to label an antigen or an antibody, or a nucleic acid for electrochemiluminescence immunoassay by immunoreaction or ECL reaction.

The structure of ruthenium pyridine according to the present invention is as follows:

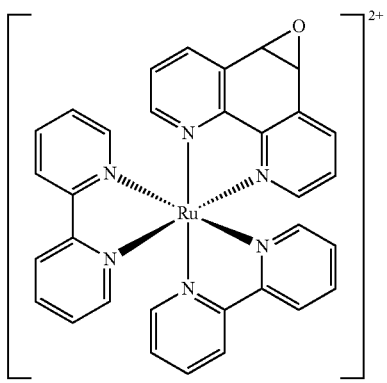

The structure of dibutyl ethanolamine is as follows:

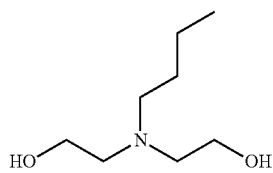

In the present invention, ruthenium pyridine is employed as a label in order to label an antigen or an antibody, and performs the electrochemiluminescence immunoassay by immunoreaction and ECL reaction. The method according to the present invention is divided into two parts, the chemical reaction and the electrochemical reaction. In some particular embodiments of the present invention, the part of chemical reaction is performed in a test tube, and the part of electrochemical reaction is performed in a flow cell.

For the specific chemiluminescence reaction triggered by electrochemistry on the surface of the electrode, an antibody is labeled by ruthenium pyridine, which is the electrochemiluminescence agent, and the solid phase carrier is coated with antigen or an antibody which forms a complex from the immunological reaction with the corresponding antigen or antibody in the sample. The complex conjugated containing the label is separated from free label by isolation. The antigen or antibody to be tested is quantitatively/qualitatively determined according to the luminescence intensity of ruthenium pyridine on the electrode.

In the present invention, magnetic particles are selected as a solid phase carrier. Due to the magnetism of the solid phase carrier, it is only required to attract with a magnet when separating the free labels from the combined labels, which is convenient and rapid to operate. In particular examples of the present invention, the solid phase carrier is polystyrene particles with magnetism having a diameter of 2.8 μm.

To test for thyroid stimulating hormone (TSH) in serum samples, in the method according to the present invention, an antibody against TSH conjugated with activated ruthenium pyridine and a TSH antibody conjugated with biotin are incubated and reacted with the serum to be tested, then the magnetic particles coated with streptavidin are added, so that the magnetic particle, the antigen to be tested, and the TSH antibody are linked together by the conjugation of the biotin with the avidin, forming a "sandwich".

In particular examples, the complex of ruthenium pyridine-antibody-antigen-biotinylated antibody-magnetic particle coated with streptavidin as formed is drawn into a flow measuring cell by a peristaltic pump. The complexes are adsorbed onto the surface of the electrode by the magnet located below the working electrode through the magnetic particles, while the free TSH antibodies, including the free biotinylated antibody and free TSH antibody bound to ruthenium pyridine, are drawn out of the measuring cell.

Dibutyl ethanolamine (DBAE) is added by a peristaltic pump, and voltage is applied to start the ECL reaction. This process is repeatedly performed on the surface of the electrode, to produce plenty of photons. The light intensity is detected by using a photomultiplier tube, and the light intensity thereof has a linear relationship with the concentration of ruthenium pyridine. Based on this, the content of TSH in the sample to be tested is determined.

In particular embodiments, the solid phase carriers employed in the present invention are magnetic polystyrene particles having a diameter of 2.8 μm, which are characterized by having a reaction area expanded by 20~30 times, thereby making the adsorption efficiency higher than a plate; and a homogeneous suspension is formed in the liquid to participate in the reaction in a way similar to a liquid phase, which greatly accelerates the reaction rate.

Streptavidin and biotin are used to amplify the effects of detection. One molecule of streptavidin can bind 4 molecules of biotin. In particular embodiments of the present invention, streptavidins are homogeneously and firmly coated on the magnetic particles, to form a general solid carrier which can bind to biotin. When a streptavidin-coated magnetic particle comes into contact with a biotinylated antigen or antibody, the antigen or antibody is immediately coated on the magnetic particle. The antigens or antibodies in a conjugated state are separated from those in free state by magnetism using an electromagnetic field. This is convenient and rapid, and full automation is achieved. Meanwhile, the recycling of the labels is achieved. In addition, luminescence time is longer, the intensity is higher, and the luminescence is easily determined.

The methods for detecting protein and polypeptide antigens are mainly double antibody sandwich method and competition method. The double antibody sandwich method is commonly used in the determination of protein macromolecular antigen. However, small molecular hormones, drugs, or the like, which have only a single epitope, are not suitable for the determination using the double antibody sandwich method, because they may have only one epitope, or the molecule is too small, and after binding to one antibody, they cannot bind to another antibody due to steric hindrance.

In the method according to the present invention, a competitive inhibition method can be further employed to detect small molecular antigens such as free triiodothyronine (FT3). The principle of the competitive inhibition method is that the antigens in the sample compete with an amount of labeled antigen to bind the solid phase antibody. When the content of the antigen in the sample is higher, the content of the labeled antigen conjugated on the solid phase is less.

In the method according to the present invention, an antigen-antibody complex labeled with ruthenium pyridine, the system of streptavidin and biotin, and di-n-butyl ethanolamine are employed, and immunoreaction and electrochemical reactions are applied to perform the detection of protein content, which is characterized by high sensitivity, high luminescence efficiency, and is an important non-radioactive immunoassay method, suitable for detecting various proteins such as tumor marker protein and hormone.

Preferably, the method according to the present invention can be used to detect the following items: triiodothyronine (T3), anti-sperm antibody (ASA), troponin I, thyroxine (T4), anticardiolipin antibody (ACA), CKMB, TSH, anti-endometrium antibody (AEA), free triiodothyronine (FT3), anti-ovarian antibody (AOA), free thyroxine (FT4), anti-trophoblast antibody (ATB), thyroid microsomal antibody (Anti-TM), anti-zona pellucida antibody (ZP), anti-thyroglobulin antibody (Anti-TG), anti-HCG antibody, human placental lactogen, thyroid peroxidase antibody (Anti-TPO), HCG, toxoplasma antibody (TOX), FSH, alpha-fetoprotein (AFP), carcinoembryonic antigen (CEA), prostate-specific antigen (PSA), free prostate-specific antigen (FPSA), cytomegalovirus antibody (CMV), luteinizing hormone (LH), herpes simplex virus antibody (HSV-1), prolactin (PRL), herpes simplex virus antibody (HSV-2), testosterone (TES), rubella virus antibody (RV), progesterone (PRO), Ferritin, toxoplasm circulating antigen (TOX-Ag), estradiol (E2), CA125, estriol (E3), CA153, CA199, HBsAg, neuron-specific enolase (NSE), HBsAb, CA50, HBeAg, $\beta$2 microglobulin, HBeAb, Coxsackie virus antibody, HBcAb, bone Gla protein (BGP), deoxypyridinoline (D-Pyr), vitamin D, insulin, type III procollagen (PCIII), C-peptide, type IV collagen, insulin antibody, laminin (LN), glucagon, hyaluronic acid (HA), glutamate decarboxylase antibody (GAD-AB), fibronectin (Fn), influenza virus B, parainfluenza virus, EB virus, measles virus, *Mycoplasma pneumoniae, Mycobacterium tuberculosis, Aspergillus fumigatus*, mumps virus, HCV virus, influenza virus A, human immunodeficiency virus (HIV), *Chlamydia pneumoniae*, adenovirus, respiratory syncytial virus (RSV), Echovirus, and pro-gastrin-releasing peptide, CYFRA21-1, AFP, APT, CA242, CA724, CA50, f-PSA, t-PSA, Free $\beta$-hCG, and SCCA.

AFP and APT are markers for hepatocellular carcinoma and germ cell tumor, which are also found in other related tumors such as embryonic cell cancer, ovarian teratoma, gastric cancer, biliary tract carcinoma, pancreatic cancer and the like.

CEA is a broad-spectrum marker for digestive tract tumors, and is also found in other related tumors such as lung cancer, breast cancer, medullary thyroid carcinoma and the like.

CA242 is a marker for pancreatic cancer, gastric cancer, colon cancer, and is also found in other related tumors: liver cancer, esophageal cancer, and lung cancer.

CA125 is a marker for ovarian cancer, and is also found in other tumors such as lung cancer, pancreatic cancer, breast cancer, liver cancer, gastrointestinal malignancy, and uterine cancer.

CA199 is a marker for pancreatic cancer, bile duct cancer, colorectal cancer, and is also found in other related tumors such as liver cancer, gallbladder carcinoma, bile duct cancer and the like.

CA153 is a preferred marker for breast cancer, and can increase in other related tumors such as lung cancer, ovarian cancer, lung cancer, colorectal cancer and the like.

CA724 is one of the optimal tumor markers for gastric cancer, and can be detected in other related tumors such as gastrointestinal cancer, breast cancer, lung cancer, ovarian cancer and the like, with various detection rates.

CA50 is a marker for pancreatic cancer and colorectal cancer, and is also found in other related tumors such as gastric cancer, gallbladder carcinoma, liver cancer, lung cancer, and breast cancer.

The main related tumor for NSE and pro-gastrin-releasing peptide is small cell lung cancer, and they are also found in other related tumors: lung adenocarcinoma and large cell lung cancer.

The main related tumors for CYFRA21-1 are lung squamous cell carcinoma, cervical cancer, esophageal cancer, and it is also found in other related tumors such as bladder cancer, nasopharyngeal carcinoma, ovarian cancer, and gastrointestinal cancer.

The main related tumor for f-PSA and t-PSA is prostate cancer, and they are also found in other related tumors such as certain gynecologic tumors and breast cancer.

The main related tumors for Free $\beta$-hCG are gynecologic tumors and non-spermatogonial testicular cancer, and it is also found in other related tumor such as breast tumor, spermatogonial testicular cancer, lung cancer, liver cancer and the like.

The main related tumor for SCCA is cervical squamous cell carcinoma, and it is also found in other related tumors such as lung squamous cell carcinoma, head and neck squamous cell carcinoma, esophageal cancer, and genital squamous cell carcinoma and the like.

$\beta$2-MG is an auxiliary marker for malignancy, and is especially apparent in chronic lymphocytic leukemia, lymphosarcoma, multiple myeloma and the like, and is also found to be increased in lung cancer, breast cancer, gastrointestinal cancer and cervical cancer.

The present invention further provides a kit for electrochemiluminescence immunoassay, comprising the following components: a ruthenium pyridine-labeled primary antibody against the protein to be tested, a biotinylated secondary antibody against the protein to be tested, streptavidin-coated magnetic particles, and a di-n-butyl ethanolamine solution.

In addition, the kit according to the present invention may further comprise a washing solution.

Moreover, the washing solution may be 0.05% Tween-20 in 0.05 mol/L phosphate buffer (pH 7.4). When the pH value is high, the luminescence efficiency of the photochemical reaction is high, while when the pH is low, the detection results are stable. The inventor of the present invention has found, when the pH value of the washing solution is 7.4, luminescence is efficient and stable, which fulfills the requirement for the determination of clinical samples.

The kit according to the present invention can greatly save the amount of antigen and antibody. The luminescence intensity of the photochemical reaction between dibutyl ethanolamine with ruthenium pyridine is 6 times of that produced by using tripropylamine, and thus more photons are collected by the photomultiplier tube, so that the sensitivity of the kit is higher. Values can be detected even if using a quite small amount of antigen and antibody, so that the amount of antibody can be effectively reduced, and the cost of the kit is reduced by 10%~30%.

Compared with the prior art, the electrochemiluminescence immunoassay method and kit according to the present invention have the following advantages:

1. The application of streptavidin and biotin greatly increases the sensitivity, which can reach a level of pg/ml or pmol.
2. Strong specificity, good reproducibility, CV<5%.
3. Wide detection range, which can reach 7 orders of magnitude.
4. Stable reagents without toxicity.
5. Reaction time is short, and the assay can be completed within 20 min.

DETAILED EMBODIMENTS

The present invention discloses an electrochemiluminescence immunoassay method. Those skilled in the art can use the contents herein for reference, and achieve by appropriately improving the technological parameters. Specifically, all the similar substitutions and modifications are obvious to those skilled in the art, and they are all deemed to be included within the present invention. The methods and applications of the present invention have been described by way of preferred examples, and the methods and applications described herein can be modified or appropriately changed or combined by a skilled artisan to achieve and apply the technique of the present invention without departing from the contents, spirit and scope of the present invention.

In order for a better understanding of the technical solution of the present invention by those skilled in the art, the present invention is further described below in combination with detailed examples.

Example 1: The Components of the Kit According to the Present Invention

The kit according to the present invention comprises the following components:

Reagent A. A primary antibody against the protein to be tested, labeled by the electrochemiluminescence agent ruthenium pyridine;

Reagent B. A biotinylated secondary antibody against the protein to be tested;

Reagent C. Magnetic particles coated with streptavidin, in which said magnetic particles are polystyrene particles having a diameter of 2.8 μm; and Reagent D. Dibutyl ethanolamine solution.

Preferably, a washing solution, more preferably 0.05 mol/L phosphate buffer (pH 7.4) and 0.05% TWEEN-20, can be also included. The washing solution can also be formulated by those ordinary skilled in the art by themselves.

When used, the antibody conjugated with ruthenium pyridine and the antibody conjugated with biotin in the kit according to the present invention were incubated and reacted with the sample to be tested. Then, the magnetic particles coated with streptavidin were added. The magnetic particles, the antigen and the antibody to be tested were linked together through the binding of the biotin to the streptavidin, so as to form a "sandwich" complex.

Figure 1:
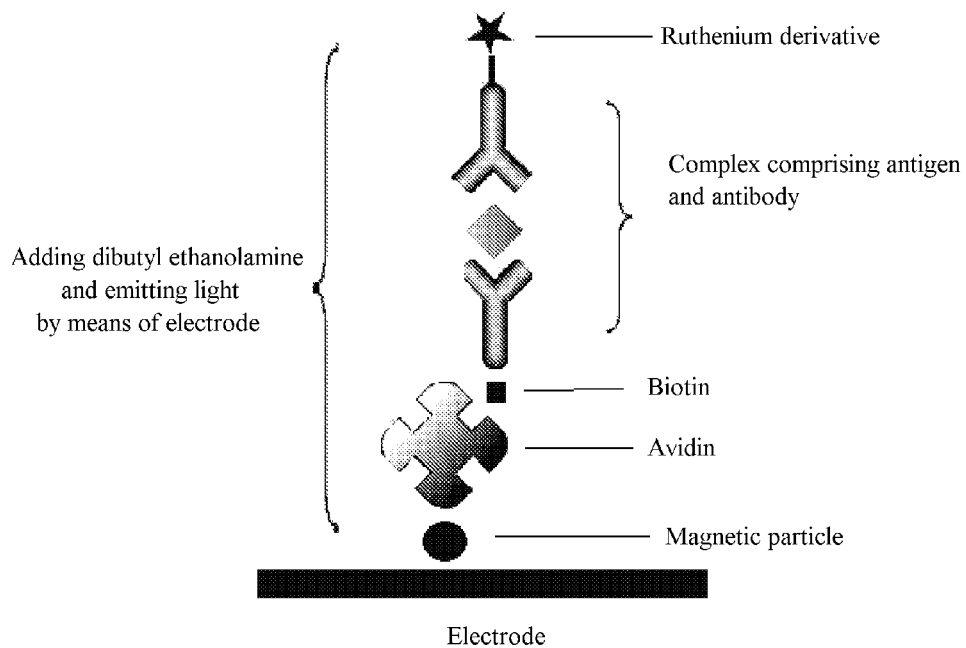
FIG. 1 is a schematic diagram of the principle of the electrochemiluminescence immunoassay method according to the present invention.

The complex was attracted onto the surface of the electrode by the magnet located below the working electrode through the magnetic particles. The label-conjugated complexes were separated from the free labels using electromagnetic field separation by means of the magnetism of iron oxide. Then, dibutyl ethanolamine (DBAE) was added, and voltage was applied to start the ECL reaction. The luminescence substrate ruthenium pyridine and dibutyl ethanolamine as a reaction component lost electrons on the surface of the electrode, so as to be oxidized. Dibutyl ethanolamine as the electron donor lost one $H^+$ to become a strong reducing agent, which reduced the trivalent ruthenium in oxidized form into an excited divalent ruthenium, the latter then releases photons and return to the luminescence substrate in the ground state. This process was performed repeatedly on the surface of the electrode, to produce plenty of photons. Light intensity was detected by using a photomultiplier tube. The light intensity thereof has a linear relationship with the concentration of ruthenium pyridine. The antigen or antibody to be tested was quantitatively/qualitatively detected, based on the light intensity emitted by ruthenium pyridine on the electrode. The schematic diagram of the above reaction principle is shown in FIG. 1.

Example 2: Detection of Human Thyroid Stimulating Hormone TSH which was Preformed Using the Method According to the Present Invention The kit comprises the following components:
Reagent A. TSH antibody labeled by ruthenium pyridine;
Reagent B. Biotinylated secondary antibody against TSH;
Reagent C. Magnetic particles coated with streptavidin;
Reagent D. Dibutyl ethanolamine solution; and
Reagent E. Washing solution.

Steps for Detection:

(1) Reagents A and B, and sample serum to be tested were added into a test tube, and reacted under a liquid phase condition at 37° C. for 8 min.

(2) Reagent C was added into the above reaction liquid, and reacted under a near liquid phase condition at 37° C. for 8 min.

(3) The reaction liquid in the test tube after the completion of the two-step reaction was introduced into a flow cell.

The flow cell is the location for all the electrochemiluminescence reactions during the process of electrochemiluminescence. One excited electrode is located under the flow cell, two detecting electrodes are installed at both sides above the excited electrode, and there is a collecting port for the photomultiplier tube to facilitate the collection and analysis of light signals. A moveable magnet is installed under the flow cell for the attraction of the magnetic particles. The reaction liquid is pumped into the flow cell by a peristaltic pump. The magnetic particles are attracted onto the electrode due to the attraction of the magnet, and the other reactants flow out of the flow cell, so as to achieve the separation of free labeled-antibodies from the conjugated labeled-antibodies.

(4) The Reagent D (dibutyl ethanolamine solution) was introduced into a flow cell, and filled the flow cell.

(5) The magnet was removed, and the electrode was electrified.

The electrochemical reaction between ruthenium pyridine and dibutyl ethanolamine took place, and the light emitted was collected by the photomultiplier tube, so that the light intensity was determined.

Figure 2:
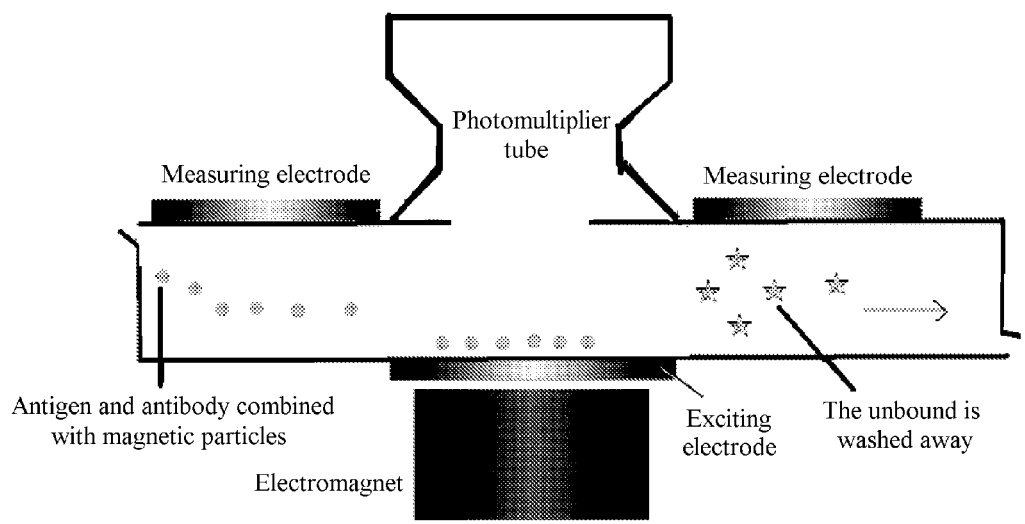
FIG. 2 is a schematic diagram of the electrochemical detection performed by the electrochemiluminescence immunoassay method according to the present invention.

The schematic diagram of the reaction in the flow cell is shown in FIG. 2.

Figure 3:
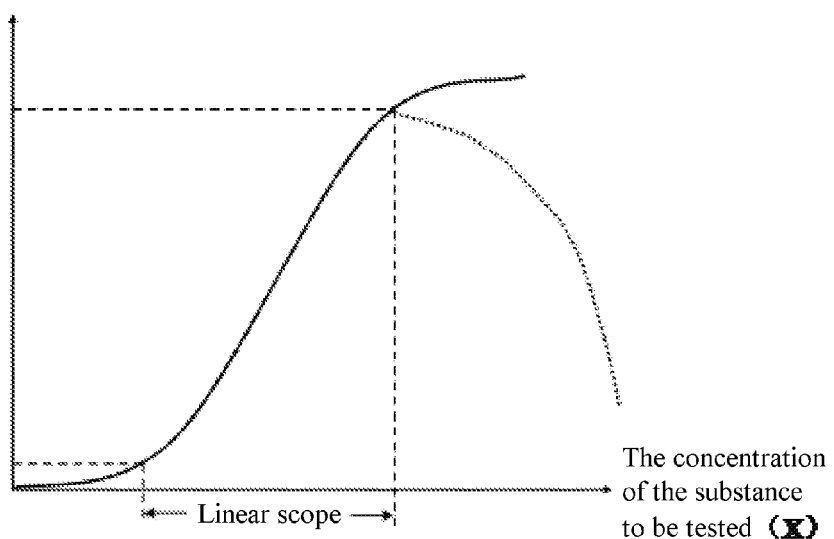
FIG. 3 is a dose-response curve for the sandwich method.

(6) Standard solutions in a gradient of concentrations were formulated, and a dose-response curve was plotted according to the logarithm of changes in the value of luminescence intensity and the logarithm of concentration, as shown in FIG. 3, and the concentrations of the protein to be tested in the samples to be tested were obtained by calculation.

(7) The voltage was terminated, and the magnetic particles were removed. Reagent E (the washing solution) was added to rinse the flow measuring chamber, and then the next sample can be determined.

A dose-response curve was plotted according to the logarithm of changes in the value of luminescence intensity and the logarithm of concentration, and it was found that they are in a good linear relationship. The concentration of TSH in the sample was extrapolated according to the dose-response curve.

Example 3: Detection of Alpha-Fetoprotein Performed by Using the Method According to the Present Invention Human serum, magnetic particles conjugated with avidin, antibody 1 conjugated with biotin, and antibody 2 conjugated with ruthenium pyridine were added into a reaction vessel. The vessel was incubated at 37° C. for 9~17 min. Magnetic separation was performed, and that is, the unconjugated material was washed away, and the above-mentioned remaining liquid comprising antigen-antibody complex containing magnetic particles was introduced into the flow cell. Dipropyl ethanolamine was added, and redox reaction took place in the presence of the electrode. During this process, light was emitted. Photons were captured by the photomultiplier tube, and analyzed and amplified by a computer. Standard solutions in a gradient of concentrations were formulated, and a dose-response curve was plotted according to the logarithm of changes in the value of luminescence intensity and the logarithm of concentration. The results were calculated. Accordingly, the contents of alpha-fetoprotein in the serum to be tested were determined.

Example 4: Detection of Carcinoembryonic Antigen Performed by Using the Method According to the Present Invention The kit comprises the following components:
Reagent A. Ruthenium pyridine-labeled antibodies against carcinoembryonic antigen;
Reagent B. Biotinylated secondary antibody against carcinoembryonic antigen;
Reagent C. Magnetic particles coated with streptavidin;
Reagent D. Dibutyl ethanolamine solution; and
Reagent E. Washing solution: 0.05 M phosphate buffer (pH 7.4) and 0.05% Tween-20.
Steps for Detection:
(1) Reagents A and B, and sample serum to be tested were added into a test tube, and reacted under a liquid phase condition at 37° C. for 8 min.
(2) Reagent C was added into the above reaction liquid, and reacted under a near liquid phase condition at 37° C. for 8 min.
(3) The reaction liquid in the test tube after the completion of the two-step reaction was introduced into a flow cell.
(4) The dibutyl ethanolamine solution was introduced into a flow cell, and filled the flow cell.
(5) The magnet was removed, and the electrode was electrified. The electrochemical reaction between ruthenium pyridine and dibutyl ethanolamine took place, and the light emitted was collected by the photomultiplier tube, so that the light intensity was determined.

(6) Standard solutions in a gradient of concentrations were formulated, and a dose-response curve was plotted according to the logarithm of changes in the value of luminescence intensity and the logarithm of concentration, and the concentrations of the antigen to be tested in the samples to be tested were obtained by calculation.
(7) The washing solution was introduced into the flow cell to thoroughly rinse the reactants so that the next sample can be determined.

Example 5: Detection of Free Triiodothyronine (FT3) Using the Competition Method The methods for detecting protein and polypeptide antigens are mainly double antibody sandwich method and competition method. The double antibody sandwich method is commonly used in the determination of protein macromolecular antigen. However, small molecular hormones, drugs, or the like, which have only a single epitope, are not suitable for the determination using the double antibody sandwich method, because they may have only one epitope, or the molecule is too small, and after binding to one antibody, they cannot bind to another antibody due to steric hindrance.

In the method according to the present invention, a competitive inhibition method was employed to detect small molecular antigens such as free triiodothyronine (FT3). The principle of the competitive inhibition method is that the antigens in the sample are competed with an amount of labeled antigen to bind the solid phase antibody. When the content of the antigen in the sample is higher, the content of the labeled antigen conjugated on the solid phase is less.

Figure 4:
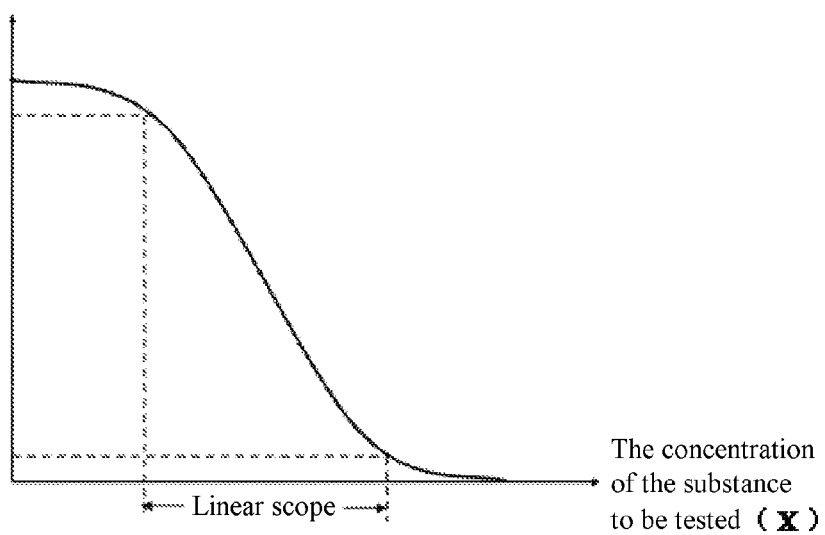
FIG. 4 is a dose-response curve for the competition method.
Figure 5:
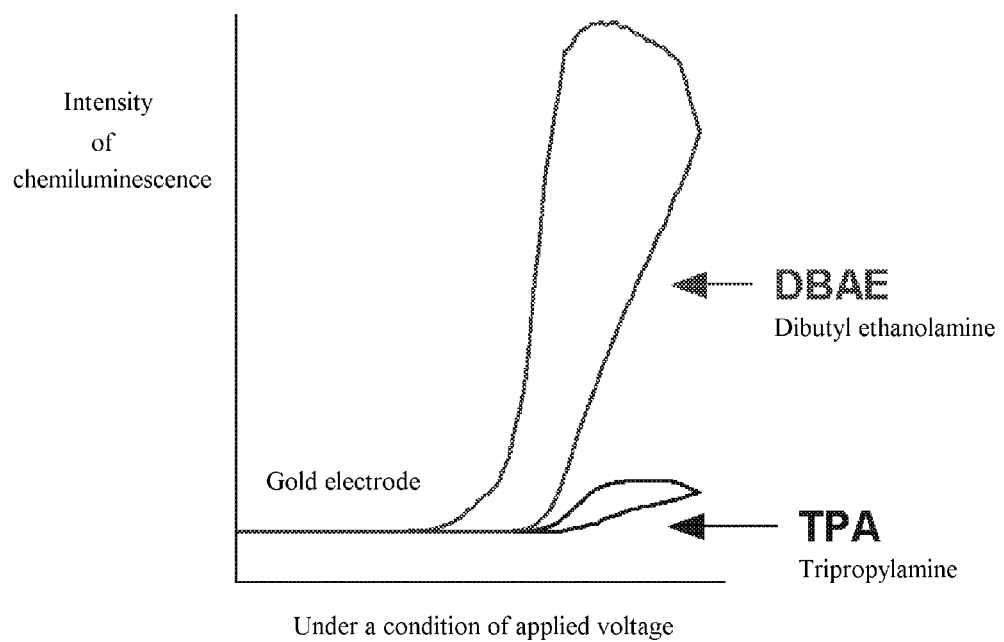
FIG. 5 is a diagram in which the luminescence intensities of dibutyl ethanolamine and tripropylamine on a platinum electrode and a gold electrode are compared.

The kit comprises the following components:
Reagent A. FT3 antigen labeled by ruthenium pyridine;
Reagent B. Biotinylated antibody against FT3 antigen;
Reagent C. Magnetic particles coated with streptavidin;
Reagent D. Dibutyl ethanolamine solution; and
Reagent E. Washing solution: 0.05 M phosphate buffer (pH 7.4) and 0.05% Tween-20.
Steps for Detection:
(1) Reagents A and B, and sample serum to be tested were added into a test tube, and reacted under a liquid phase condition at 37° C. for 8 min.
(2) Reagent C was added into the above reaction liquid, and reacted under a near liquid phase condition at 37° C. for 8 min.
(3) The reaction liquid in the test tube after the completion of the two-step reaction was introduced into a flow cell.
(4) The dibutyl ethanolamine solution was introduced into a flow cell, and filled the flow cell.
(5) The magnet was removed, and the electrode was electrified. The electrochemical reaction between ruthenium pyridine and dibutyl ethanolamine took place, and the light emitted was collected by the photomultiplier tube, so that the light intensity was determined.
(6) Standard solutions in a gradient of concentrations were formulated, and a dose-response curve was plotted according to the logarithm of changes in the value of luminescence intensity and the logarithm of concentration, as shown in FIG. 4 and the concentrations of the antigen to be tested in the samples to be tested were obtained by calculation.
(7) The washing solution was introduced into the flow cell to thoroughly rinse the reactants so that the next sample can be determined.

Example 6: Determination of Sensitivity and Detection Limit of the Method According to the Present Invention A UDECL electrochemiluminescence analyzer was used. The high voltage of the photomultiplier tube was set to be 900 v, the scanning voltage was 0.2~1.6 v, the scanning speed was 150 mV/s, and the working electrode employed was a Pt electrode. The buffer was 0.05 M phosphate buffer (pH 7.4) and 0.05% Tween-20. The luminescence signal of the solution was detected, to determine the detection limit of the method according to the present method.

Standard solutions in a gradient of concentrations were formulated, and a dose-response curve was plotted according to the logarithm of changes in the value of luminescence intensity and the logarithm of concentration, and it was found that they were in a good linear relationship.

The sensitivity of the enzymic detection method of chemiluminescence immunoassay, such as the reaction system of alkaline phosphatase and horseradish peroxidase with luminol, was generally 0.12 mIU/L; the detection scope of the sensitivity of conventional electrochemical methods is 0.005~100 μIU/ml, and the detection scope of the method according to the present invention is 0.001-100 μIU/ml. The detection scope of the electrochemiluminescence immunoassay of the electrochemiluminescence method is wider than that of the ELISA.

An electrochemiluminescence immunoassay method proposed by the present invention has been described by examples, and it is obvious that modification or appropriate alteration and combination can be made to the electrochemiluminescence immunoassay method according to the present invention by those skilled in the art, without departing from the contents, spirit and scope of the invention, in order to achieve the techniques disclosed in the present invention. Specifically, it should be pointed out that all the similar substitutions and modifications are obvious to those skilled in the art, and they are all deemed to be within the spirit, scope and contents of the present invention.

The invention claimed is:

1. An electrochemiluminescence (ECL) immunoassay method comprising:
   step 1 of (i) reacting a ruthenium pyridine-labeled primary antibody that binds to a protein of interest with a biotinylated secondary antibody that binds to the protein of interest and with a sample, or (ii) reacting a ruthenium pyridine-labeled antibody that binds to a protein of interest with a biotinylated protein of interest and with a sample;
   step 2 of adding magnetic particles coated with streptavidin to the mixture of step (a) to form a complex comprising the protein of interest, the antibody and the magnetic particle which is then transferred into a flow cell, wherein the complex is adsorbed onto the surface of an electrode through the magnetic particle;
   step 3 of adding a dibutyl ethanolamine solution and applying voltage to the mixture of step (b) to initiate an ECL reaction, and collecting scanned optical signals with an optical detector; and
   step 4 of providing solutions having a gradient of concentrations of the protein of interest, performing steps 1-3 on these solutions, and plotting a dose-response curve according to the logarithm of changes in the value of luminescence intensity and the logarithm of concentration, thereby obtaining the concentration of the protein of interest in the sample;
   wherein the structure of ruthenium pyridine is

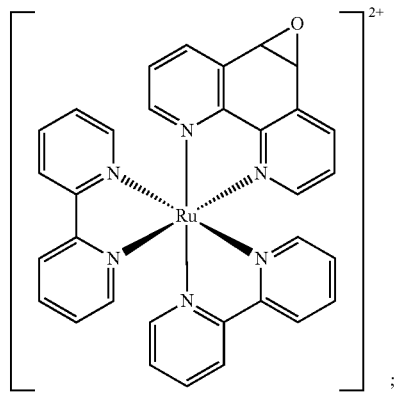

;
   wherein the magnetic particle is a polystyrene particle having a diameter of 2.8 μm;
   wherein step 1 is performed under a liquid phase condition at 37° C. for 8 min, and step 2 is performed under a near liquid phase condition at 37° C. for 8 min,
   wherein the protein of interest is Thyroid-stimulating hormone ("TSH"), free triiodothyronine ("FT3"), or carcinoembryonic antigen ("CEA").

2. The electrochemiluminescence immunoassay method according to claim 1, wherein the sample is serum, urine, or tissue fluid.

* * * * *